United States Patent [19]
Geraci et al.

[11] Patent Number: 5,952,492
[45] Date of Patent: Sep. 14, 1999

[54] CHEMICAL SYNTHESIS OF EXOCHELINS

[75] Inventors: Leo S. Geraci; Stuart G. Levy; James P. Hudspeth; Richard L. Buswell; Jay F. Stearns, all of Santa Rosa, Calif.

[73] Assignee: Keystone Biomedical, Inc., Los Angeles, Calif.

[21] Appl. No.: 09/134,457

[22] Filed: Aug. 14, 1998

[51] Int. Cl.⁶ .................................................. C07D 413/12
[52] U.S. Cl. ............................................................ 540/524
[58] Field of Search ............................................. 540/526

[56] References Cited

U.S. PATENT DOCUMENTS

| | | | |
|---|---|---|---|
| 5,721,209 | 2/1998 | Horwitz et al. | 514/11 |
| 5,786,326 | 7/1998 | Horwitz et al. | 514/11 |
| 5,837,677 | 11/1998 | Horwitz et al. | 514/11 |

OTHER PUBLICATIONS

Mauer et al. (J. Am. Chem. Soc. 1983, 105(3), 240–245).
Hu et al. (J. Am. Chem. Soc. 1997, 119(15), 3462–3468).

*Primary Examiner*—Mukund J. Shah
*Assistant Examiner*—Bruck Kifle
*Attorney, Agent, or Firm*—Loeb & Loeb LLP; Michael J. Ram

[57] ABSTRACT

A process for the synthetic generation of high affinity, iron binding compounds known as Exochelins, and more particularly, to a synthetic process for making Exochelins and to modifications to these newly synthesized compounds to vary their physiological properties, including applications of these newly synthesized and utile compounds for diagnosing and treating disease in mammals.

2 Claims, 5 Drawing Sheets

11B

CHEMICAL SYNTHESIS OF EXOCHELINS

BACKGROUND OF THE INVENTION

The present application expressly incorporates by reference U.S. Ser. No. 08/383,180, now U.S. Pat. No. 5,721,209, U.S. Ser. No. 08/796,791, now U.S. Pat. No. 5,786,326, U.S. Ser. No. 08/882,122; and U.S. Ser. No. 08/960,714, all to Horwitz, et al., all of which are subject to an exclusive license or assignment to the same assignee as this application.

The present invention relates to a heretofore undisclosed process for the synthetic generation of high affinity, iron binding compounds known as Exochelins, and more particularly, to a synthetic process for making Exochelins and to modifications to these newly synthesized compounds to vary their physiological properties, including applications of these newly synthesized and utile compounds for diagnosing and treating disease in mammals.

The above referenced U.S. patents and applications have shown that exochelins have unique physiological benefits. For example, in acute myocardial infarction, cardiac tissue is damaged by two sequential events, hypoxia in the ischemic phase and oxidative damage in the reperfusion phase. Myocardium damaged in the ischemic phase can be salvaged by reintroduction of blood into the ischemic area. However, reperfusion can result in injury to the reperfused tissue as a result of an inflammatory response caused by the migration of leucocytes into the tissue and the production of reactive oxygen species. One of the most reactive species is the hydroxyl radical (—OH) which is generated in the presence of iron, and which often results in cell death or related oxidative tissue damage.

Prevention of the formation of (—OH) prevents lethal cell damage by several mechanisms. It is well known that the formation of (—OH) is dependent on the presence of free iron, and that iron chelators will prevent reperfusion injury. For example, the iron chelator deferoxamine, when administered prior to reperfusion, prevents injury and reduces myocardial infarct size during coronary artery occlusion and reperfusion. However, reperfusion injury occurs rapidly after the reestablishment of blood flow to the ischemic myocardium.

The formation of the (—OH) radical is dependent on the presence of free iron and iron chelators can scavenge the free iron and thus render the iron unavailable to catalyze the hydroxyl radical formation. However, prior known chelating means either do not prevent (—OH) production by the Fenton Reaction (i.e., EDTA), or enter the cells too slowly (i.e., desferrioxamine). As a result, sufficient quantities of the chelating agent are not available to act rapidly enough to chelate enough iron to prevent the formation of (—OH) and cell damage and destruction which results.

Desferoxamine has been demonstrated to be effective if administered prior to occurrence of the myocardial infarct but to be ineffective if administered at or after the onset of reperfusion. Similar injury to heart tissue can occur as a result of heart bypass procedures, such as during open heart surgery, or to other body organs when they are deprived of oxygenated blood as a result of surgery or injury. Thus, iron scavenging chelators are clearly needed to prevent oxidative tissue damage.

Prior to the discoveries of Horwitz, et al., compounds referred to as Exochelins had been briefly described, and their general function in the growth of mycobacteria was likewise discussed by Macham, Ratledge and Barclay at the University of Hull in England (MACHAM, L. P., RATLEDGE, C. and NOCTON J. C., "Extracellular Iron Acquisition by Mycobacteria: Role of the Exochelins and Evidence Against the Participation of Mycobactin", *Infection and Immunity,* December 1975, pp.1242–1251, Vol. 12, No. 6; BARCLAY, R. and RATLEDGE, C., "Mycobactins and Exochelins of *Mycobacterium tuberculosis, M. bovis, M. africanum* and Other Related Species", *Journal of General Microbiology,* 1988, pp.134, 771–776; MACHAM, L. P. and RATLEDGE, C., *Journal of General Microbiology,* 1975, pp. 89, 379–382).

Macham identified the existence of a substance found in the extracellular fluid, which he referred to as 'exochelin'. Macham further described the materials he referred to as exochelins as water and chloroform soluble compounds having the ability to chelate free iron. Macham, et al., did not isolate or purify the compounds, merely characterizing them as penta- or hexapeptide, with molecular weights in the range of 750 to 800, inter alia.

According to Macham's work, his exochelins have similarities to mycobactin—which is located in the cell wall and functions to transmit iron to the interior of the cell. However, unlike mycobactin, a lipophilic, water insoluble molecule which is unable to diffuse into, and assimilate free iron from the extracellular environment, Exochelin functions at physiological pH to sequester iron from other iron bearing compounds in the serum. Also, depending on the bacterial source of the compounds, Macham, et al. disclosed that his molecules may also include salicylic acid or beta-alanine.

Barclay et al. (Ibid.) likewise described the production of compounds he called exochelins from twenty-two different strains of *M. tuberculosis* and related species. However, neither these, nor any other known prior investigators, determined the specific structure of those compounds, or identified any application for the same outside of their function as a transport medium for iron to mycobactin located in the cell wall.

In sum, Macham et al. recognized that after sequestering iron from, for example, ferritin or transferrin (and the like iron bearing compounds found in the serum) his compounds present the iron in a form that can be transferred to mycobactin, while Barclay et al. described production of his compounds from known mycobacterial strains without precisely elucidating their structure.

The total synthesis of a related compound, Mycobactin S2, was reported by Maurer and Miller in 1983 (MAUER, P. J. and MILLER, M. J. "Total Synthesis of a Mycobactin: Mycobactin S2", 1983, *J. Am. Chem. Soc.,* pp. 240–245, Vol. 105). Mauer et al. successfully prepared 29 milligrams of a Mycobactin utilizing a complex, multi-step synthetic pathway. Mycobactin S2, however, is significantly different from the target molecule according to the synthesis of the present invention. Likewise, Exochelin synthesis remains unreported to date.

The following references provide teachings relevant to the synthesis according to the present invention:

MAUER, P. J. and MILLER, M. J., 1982, *J. Am. Chem. Soc.,* 104, 3096;

FARKAS, L. et al., 1967, *Tetrahedron,* 23, 741;

SCHNIEPP, L. E. and GELLER, H. H., 1946, *J. Am. Chem. Soc.,* 68, 1646;

GAUDRY, R., 1948, *Can. J. Res. Sect. B,* 26, 387;

DREYFUSS, P., 1974, *J. Med. Chem.,* 17(2), 252;

BERLINGUET, L. and GAUDRY, R., 1952, *J. Biol. Chem.,* 198, 765;

BODANSZKY, M., et al., 1978, *J. Med. Chem.,* 21(10), 1030;

MAURER, P. J. and MILLER, M. J. 1981, *J. Org. Chem. Soc.*, 46(13), 2835;

BIRNBAUM, S. M., LEVINTOW, L. KINGSLEY, R. B. and GREENSTEIN, J. P., 1952, *J. Biol. Chem.*, 194, 455;

COREY, E. J. and VANKATESWARLU, A., 1972, *J. Am. Chem. Soc.*, 94, 6190;

SIEBER, P., 1977, *Helv. Chim. Acta*, 60, 2711 (b);

GERLACH, H., 1977, *Helv. Chim. Acta*, 60, 3039;

MITSUNOBU, O., 1981, *Synthesis*, 1981, 1.

Horwitz, et al., have discovered the currently accepted structural nature of exochelins, and patented uses of the same as novel iron chelators to inhibit the iron mediated oxidant injury which occurs during reperfusion, and have applications pending to other hydroxyl radical related insults to living tissues, including cancer, arteriosclerosis, organ preservation and vessel occlusion following angioplasty.

Likewise, the synthesis of related compounds strongly suggests the medical need for, and the production of synthetic versions of such important and needed compounds. See, for example, HU, J. and MILLER, M. J., "Total Synthesis of a Mycobactin S, a Siderophore and Growth Promoter of *Mycobacterium Smegmatis*, and Determination of its Growth Inhibitory Activity against *Mycobacterium tuberculosis*", 1997, pp.3462–3468, J. Chem. Soc. 119. However, complications in synthesizing the desired compounds require modifications to known procedures, and various sterochemical constraints have prevented generating Exochelins through synthetic routes.

With chelation of iron now being recognized as a means for preventing the oxidative damage of living tissue, the potential applications for Exochelins and related compounds abound. As an iron scavenger in a physiological system capable of withdrawing iron from iron-bearing proteins, Exochelins effectively prevent cell destruction following interruption of blood flow. Similarly, chelation of other metals can regulate levels of the same in various other therapeutic settings, including the delivery of various desirable metals to the body, or the targeting of diseased organs with beneficial drugs bound to exochelins, or the like synthetic transport means.

Prior work of Horwitz, et al., resulted in purified Exochelins and demonstrated their utility as scavengers of free iron and their effectiveness in preventing the formation of tissue damaging hydroxyl radicals. In particular, Horwitz, et al., purified Exochelins from *M. tuberculosis* and demonstrated that they effectively removed iron from transferrin, lactoferrin and ferritin at physiological pH, without transmitting any of the infectious properties of the tuberculosis bacteria. Likewise, Horwitz, et al., were responsible for showing for the first time that these Exochelins block hydroxyl radical formation by the Fenton reaction and, based upon the response of cardiac myocytes, are effective for preventing reperfusion injury after myocardial infarction or vascular insults to other tissue when administered after an attack occurs, in addition to several hours following such an episode.

Further, Horwitz, et al., in eludicating the chemical structure of Exochelins noted that prior references cited above had failed to define the actual structure and, instead, characterizing the exochelins as peptides. These unsuccessful attempts to identify the actual structure of the exochelin family likewise have hindered anyone from undertaking or accomplishing their synthesis. By uncovering the broad range of molecular weights which Exochelins have, Horwitz, et al., have discovered that several series of compounds with identifiable differences in molecular weights are properly included with the grouping. Exochelins cannot be considered to be peptides; instead they contain three amino acids and other structural moieties (salicylic acid, dicarboxylic acids or monoester analogs, and hydroxy carboxylic acids) formed by amide (—NH—CO—), hydroxymate (—NH (OH)—CO—) and ester condensations (—CO—O).

Likewise, in copending U.S. Ser. No. 08/882,122 deprivation of iron has been shown to attack cancer cells by modes which are particularly well addressed by Exochelins. Owing to their very high affinity for iron and their lipid solubility, Exochelins produced from, *Mycobacterium tuberculosis* possess enhanced ability to enter cells. A synthetic iron chelator with lipid solubility clearly would help to address cancer diagnosis, treatment, and screening as well as other physiological problems addressed by use of biologically derived exochelins.

Clearly, there exists a longstanding need for an improved synthetic agent or compound effective for rapidly chelating metals as they become available, to counteract myocardial infarction, and treat cancer and other related medical conditions driven by the presence of free metals, or protect tissue which may be damaged by the hydroxyl radical and related mechanisms imparting cell death and destruction.

OBJECTS AND SUMMARY OF THE INVENTION

Accordingly, it is an object of the invention to provide a process for the synthetic preparation of Exochelins which overcomes the drawbacks of the prior art. An additional object of the invention is to synthesize a compound which behaves, in all respects, like the natural material isolated by Horwitz, et al.

An additional object of the present invention is to provide a process to prepare synthetic Desferri Exochelin 772SM(R) or (S) which rapidly chelates ferric iron in solution.

It is a further object of the invention to provide for the chemical synthesis of Desferri-Exochelin 772SM(R) or (S) effective for rapidly binding iron, among other metals.

It is an additional object of the present invention to provide a synthetically prepared Exochelin compound that elutes on reverse-phase HPLC (phenyl column) at the same concentration of acetonitrile as the native molecule.

It is yet still another object of the invention to provide a simplified process design for the generation of synthetic Exochelins on an industrial scale for use in the prevention of oxidative damage to living tissue.

Briefly stated, there is provided a synthetic process for generating Exochelin 772SM(R), a new molecule having a seven carbon chain terminating in a methyl ester coupled to an acyclic hydroxamate, with four stereogenic centers, including three S-isoforms and an R-configuration at a B subunit.

According to a feature of the present invention there is provided, a process for the synthesis of EXOCHELIN 772SM(R) comprising the steps of reacting a mixture of pimelic acid, dimethyl pimelate, hydrochloric acid, methanol and di-n-butyl ether to produce methyl hydrogen pimelate and then mixing the methyl hydrogen pimelate with thionyl chloride and dimethyl formamide to generate methylpimeloyl chloride which was stored for later reaction. This was then added to a suspension of O-benzyl hydroxylamine hydrochloride and triethyl amine in $CH_2Cl_2$ to produce O-benzylmethylpimelyl hydroxamate. To a solution of (L)-6-hydroxynorleucine and triethylamine in a tetrahydrofuran (THF)-water mixture a solution of di-tert-butyl dicarbonate in THF was added. An aqueous layer was then acidified to a pH 3 with citric acid and extracted with EtOAc. The organic layer was dried and purified to produce (L)-N-Boc-6-hydroxynorleucine (L)-N-Boc-6-hydroxynorleucine was reacted with allyl bromide to produce (L)-N-Boc-6-hydroxynorleucine allyl ester. To (L)-N-Boc-6-hydroxynorleucine allyl ester and carbon tetrabromide in anhydrous $CH_2Cl_2$ was added triphenylphosphine to provide a viscous oil. which was then added to EtOAc/hexane and (L)-N-Boc-6-bromonorleucine allyl ester was recovered. A mixture of (L)-N-Boc-6-bromonorleucine allyl ester, O-benzylmethylpimelyl hydroxamate, potassium iodide (KI) and potassium carbonate in anhydrous acetone was prepared and (L)-$N^6$-methylpimelyl-$N^6$-(benzyloxy)-$N^2$-Boc-lysine allyl ester was recovered. Trifluoro acetic acid was added to the (L)-$N^6$-methylpimelyl-$N^6$-(benzyloxy)-$N^2$-Boc-lysine allyl ester to form a solid intermediate which was added to (L)-N-(2-(benzyloxy)benzoyl)serine and 2-ethoxy-1-ethoxycarbonyl-1,2-dihydroquinoline to produce a light brown viscous oil identified as (L)-$N^6$-Methylpimelyl-$N^6$-(benzyloxy)-$N^2$-((L)-N-(2-(benzyloxy)benzoyl) serine)-lysine allyl ester. Thionyl chloride was gradually added to a cooled ($^-30°$ C. bath) solution of the lysine allyl ester in anhydrous tetrahydrofuran (THF) and the golden colored oil was then purified to provide a light brown viscous oil identified as (L)-M-Methylpimelyl-$N^6$-(benzyloxy)-$N^2$-((S)-2-(2-benzyloxy) phenyl)-2-oxazoline4-carbonyl)-lysine allyl ester. To the solution of oxazoline-lysine allyl ester in anhydrous $CH_2Cl_2$ was added morpholine and tetrakis (triphenylphosphine) palladium to provide an acid. To a solution of acid and (L)-$N^\alpha$-((S)-3-hydroxybutyryl)-$\alpha$-amino-N-(benzyloxy) caprolactam in anhydrous THF was gradually added diethyl azodicarboxylate. The material isolated was mixed with MeOH, palladium and hydrogen. The mixture was filtered and the solvent was subsequently removed under reduced pressure and co-evaporated with $CH_2Cl_2$ to provide an off-white flaky solid determined by NMR analysis indicated to be Exochelin 772SM(R) shown as formula 1a.

The above, and other objects, features and advantages of the present invention will become apparent from the following description read in conjunction with the accompanying figures, tables and formulae, outlining and describing a set of embodiments of synthetic processes according to the present invention, wherein like reference designating numerals are employed throughout to represent common chemical species moieties and functional groups.

BRIEF DESCRIPTION OF THE DRAWINGS

These and other features, aspects and advantages of the present invention will become better understood with reference to the following description, appended claims, and accompanying drawings, where:

DETAILED DESCRIPTION OF THE INVENTION

The present inventors have discovered, as described in the above referenced copending applications and U.S. Letters Patents, that Exochelins have been found to block or significantly reduce oxidative damage to tissue resulting from the iron-mediated catalysis of tissue and free radical reactions mediated by the hydroxyl radical. In particular, such effects have been shown to be at least participative in reperfusion injury, arteriosclerosis cataract formation, cancer and other degenerative injuries to living tissue.

Likewise, Exochelins have been shown to effectively prevent, or at least retard, reperfusion injury when administered at the start of, or concurrent with, reperfusion, significantly reduce or prevent arterial blockage following angioplasty, and reduce the damage to normal tissue resulting from chemotherapy used to treat cancer. Further, the present inventors have previously disclosed that the Exochelins comprise a much broader class of materials having a different chemical structure than those originally theorized by Macham et al. and Barclay et al.

Exochelins are now known to chelate a broad range of metals, and when properly modified they can be used to treat specified diseases, attack cancer cells (among others) and assist in diagnostic and monitoring functions by detecting the presence of disease. For example, neuroblastoma cells can be negatively affected by the removal of iron using desferrioxamine with harmful impacts upon healthy tissue. Likewise, chemotherapy, such as used during leukemia, often results in iron overload (as do transfusions) and Exochelins have been shown to be effective for treating the same.

Figure 1A:
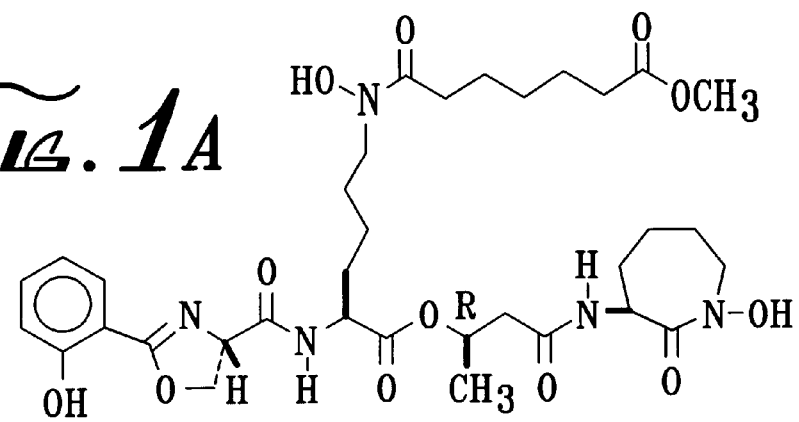
FIG. 1a is the target molecule EXOCHELIN 772SM in its R or S configuration.
Figure 1B:
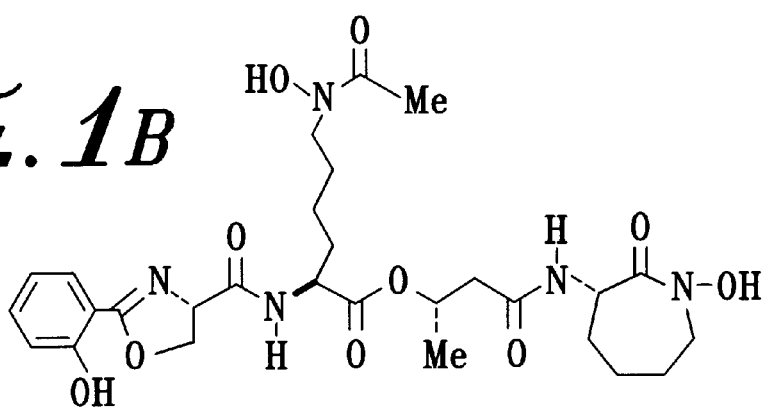
FIG. 1b is Myobactin S2 shown for comparison purposes.

Referring now to the figures, and more particularly to FIG. 1a showing the target molecule Exochelin 772SM(R) compared to Mycobactin S2 (FIG. 1b). Although this molecule is similar in structure to Mycobactin S2, there are significant differences. Exochelin 772SM(R) possesses a six carbon chain terminating in a methyl ester coupled to the acyclic hydroxamate (subunit F, FIG. 1c), while Mycobactin S2 contains only a methyl group at the corresponding position. The other structural variation is stereochemical in nature. Each compound contains four stereogenic centers, and in the case of Mycobactin S2, all of these occur in the S-configuration. Exochelin 772SM(R), however, possesses the R-configuration in subunit B. The three remaining centers occur as the S-isoforms, analogous to Mycobactin S2. These differences require that appropriate modifications of the established procedure be employed in order to synthesize the target molecule.

Figure 1C:
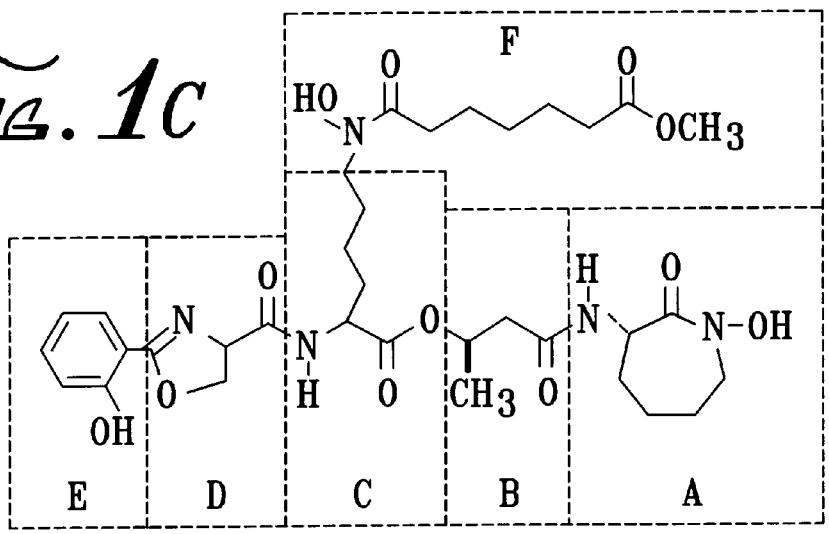
FIG. 1c depicts the target molecule of FIG. 1a separated into functional portions, designated as sections A–F, to aid in the description of the various mechanisms further explained as Schemes I–VII below.
Figure 2:
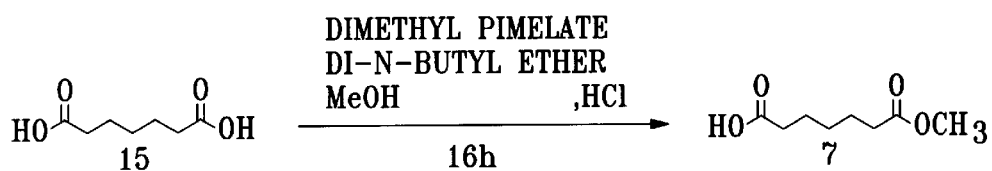
FIG. 2 shows a first portion of the chemical pathway, in accordance with an embodiment of the process for the synthesis of the present invention.
Figure 2:
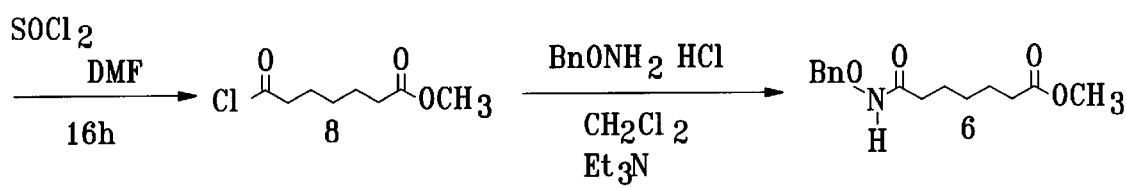
Figure 3:
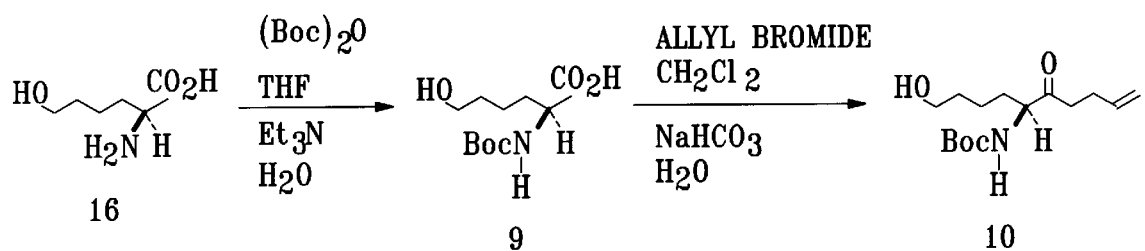
FIG. 3 shows a second portion of the chemical pathway, in accordance with an embodiment of the process for the synthesis of the present invention.
Figure 3:
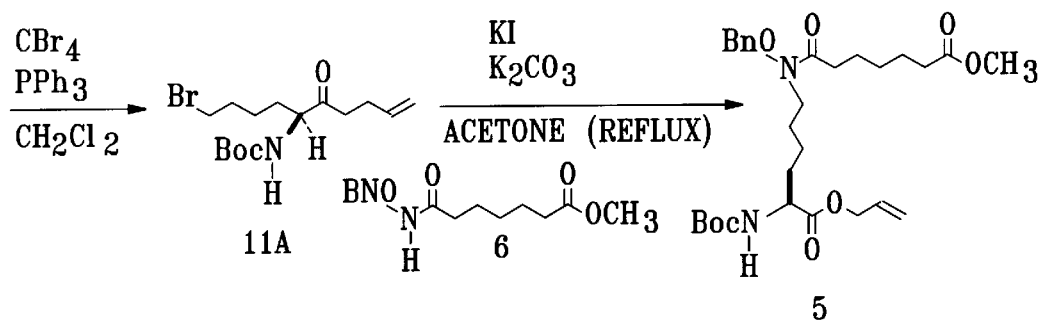
Figure 4:
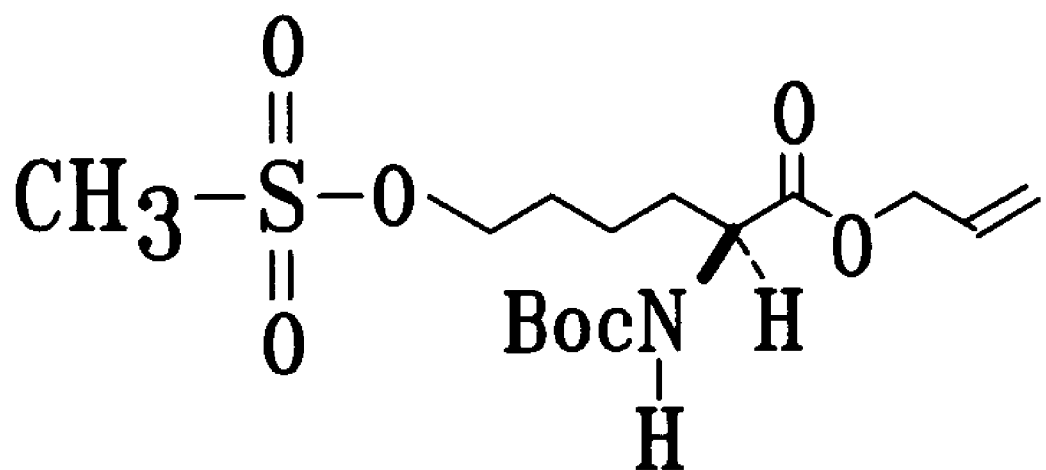
FIG. 4 shows an alternative reactant for performing a portion of the chemical pathway in accordance with an embodiment of the process for the synthesis of the present invention.
Figure 5:
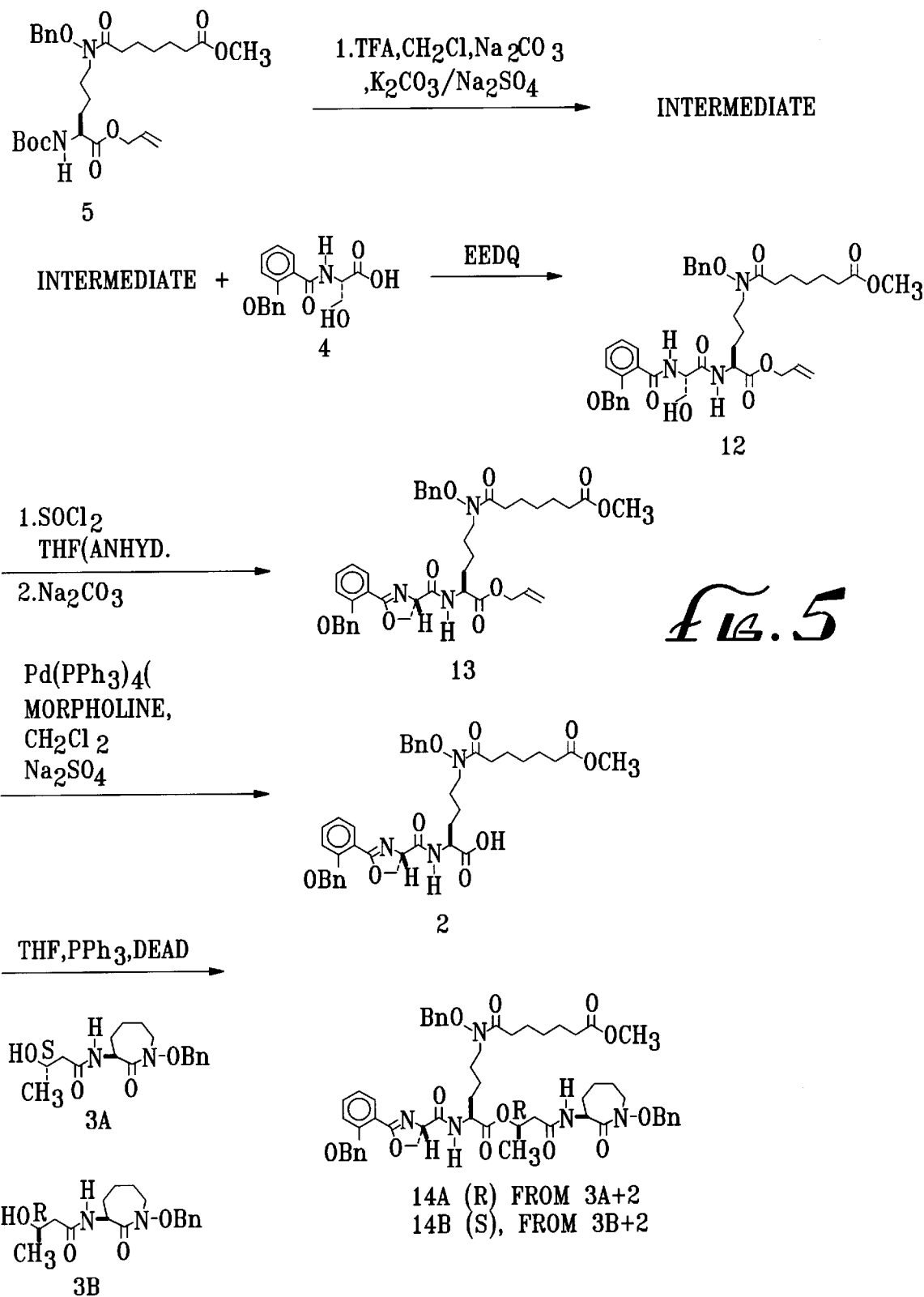
FIG. 5 shows the chemical pathway under a third portion of the chemical pathway, in accordance with an embodiment of the process for the synthesis of the present invention.
Figure 6:
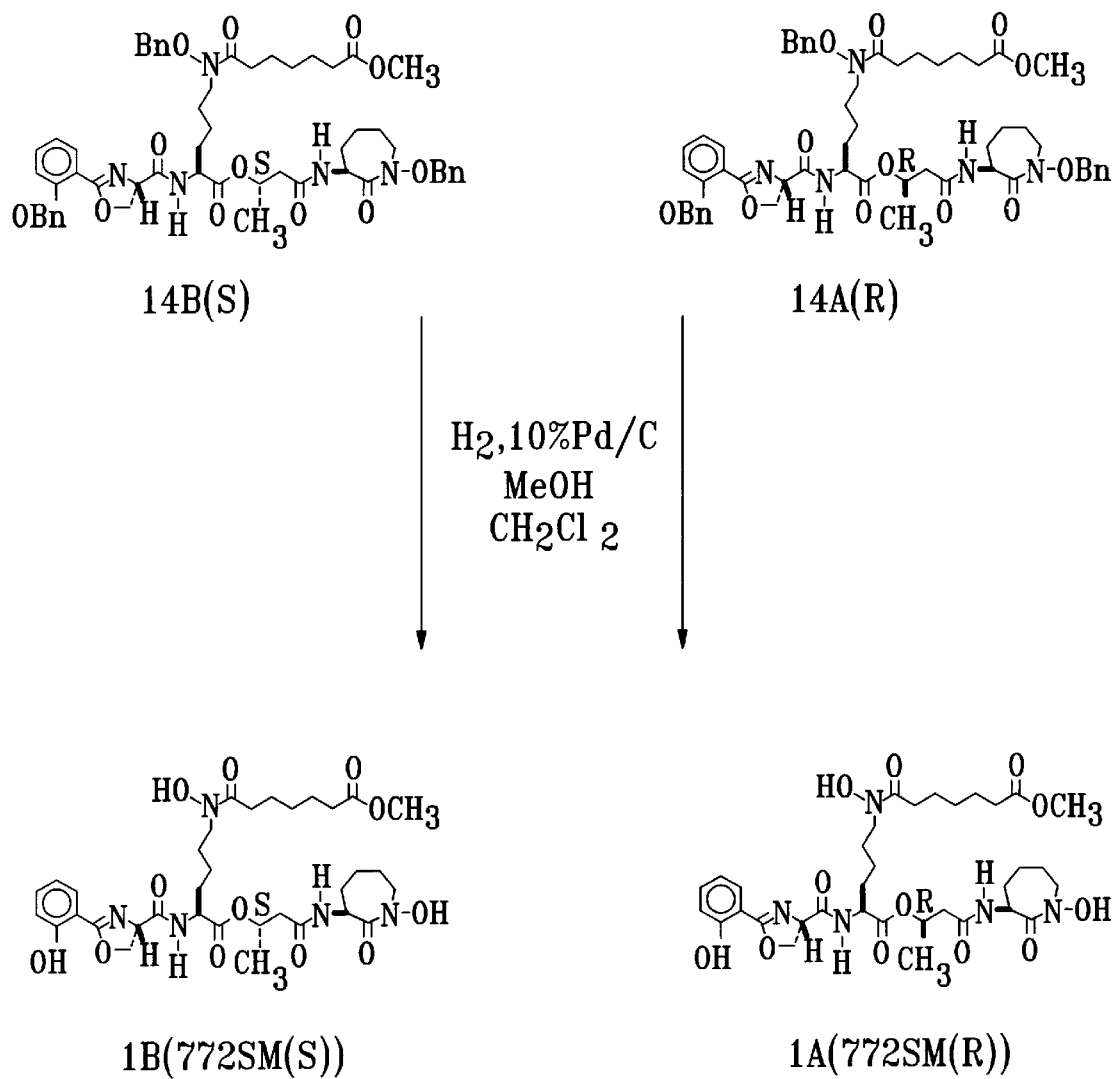
FIG. 6 shows the final step in the chemical pathway, in accordance with an embodiment of the process for the synthesis of the present invention.

Referring to FIG. 1c (and in particular to the blocked diagram of functional units of the target molecule designated A–F), the initial goal of the instant synthesis was the preparation of the E/D subunits of Exochelin 772SM(R). The Synthesis Of 772SM(R) (1a) And 772SM(S) (1b) General Summary The syntheses of 772SM(R) and 772SM(S) are similar in some respects to the published synthesis of mycobactin S2 due to their similarity in structure. The difference between diastereoisomers of 772SM is the labeled chiral center. A convergent approach was used in the total syntheses requiring twenty-two synthetic transformations.

The exochelin comprises an acid (Units CDEF) and caprolactam (Units AB) joined by an ester linkage.

A Mitsunobu coupling is used to join Units CDEF with Units AB were prepared according to the literature method in five synthetic steps starting with L-6-hydroxynorleucine. The prepared caprolactam was coupled with (S)-(+)-hydroxybutyric acid to form Unit AB The preparation of the acid required eight synthetic steps along the longest linear sequence starting with L-6-hydroxynorleucine by coupling a lysine derivative, as the benzyloxy carbonyl (Boc) free amine, with a serine derivative using the coupling reagent 2-ethoxy-1-ethoxycarbonyl-1,2-dihydroquinoline (EEDQ). The selective removal of the allyl ester in the presence of the methy ester allowed for the preparation of the mono acid. (Friedrich-Bochnitschek, S., Waldmann, H., Kunz, H. *J. Org. Chem.* 1989, 54, 751.)

The serine derivative was prepared from salicylic acid and L-serine in four synthetic steps according to the published method. (Maurer, P. J., Miller, M. J. *J. Am. Chem. Soc.* 1983, 105, 240; Maurer, P. J., Miller, M. J. *J. Am. Chem. Soc.* 1982, 104, 3096). A protected hydroxamic acid, used to form Unit F, was prepared in three synthetic steps from pimelic acid. (Swann, S. Jr., Oehler, R., Buswell, R. J. *Org. Syntheses, Coll. Vol. II* 1943, 276; Cason, J. *Org. Syntheses, Coll. Vol. III* 1955, 169.)

The synthesis of the S form was similar to the synthesis of R form except (R)-(−)-hydroxybutyric acid was used in the preparation of Unit AB.

Detailed Preparation

The desired exochelin was prepared in accordance with FIGS. 2–5 as set forth below.

A. Methyl hydrogen pimelate (7)

A mixture of pimelic acid (15) (75.1 g, 0.47 mol), dimethyl pimelate (50.1 g, 0.27 mol), hydrochloric acid (8 mL, 0.1 mol), methanol (25 mL, 0.62 mol) and di-n-butyl ether (20 mL) was heated (oil bath: 100–110° C.) under $N_2$ overnight. After cooling to room temperature, EtOAc (200 mL) was added and the mixture was washed with water (2×100 mL), saturated NaCl (2×100 mL) and dried ($Na_2SO_4$). The crude oil was fractionally distilled (vigreux, 125–130° C., 0.7 mm Hg) to provide a clear oil (55.5 g, 68%, purity≅95%. Based on NMR analysis, the clear oil was determined to be methyl hydrogen pimelate (7) ($^1$H NMR)): TLC ($SiO_2$, MeOH/EtOAc/hexane (2:8:15, v/v)) $R_f$=0.25–0.34; $^1$H NMR (300 MHz, $CDCl_3$) δ3.67 (s, 3 H), 2.40–2.28 (m, 4 H), 1.72–1.58 (m, 4 H), 1.45–1.32 (m, 2 H).

B. Methylpimeloyl chloride (8)

Fifty three grams (53 g) of methyl hydrogen pimelate (7) (0.3 mol) from A above was mixed with thionyl chloride (30 mL, 0.4 mol) and dimethyl formamide (0.3 mL) were stirred with heating overnight (oil bath: 52° C.). The excess thionyl chloride was then removed by distillation. The crude oil which resulted was distilled (0.6 mm Hg, 80–90° C.) to provide a clear oil (54.1 g, 92%, purity≅95%. Based on NMR analysis, the clear oil was determined to be methylpimeloyl chloride (8) ($^1$H NMR)): $^1$H NMR (300 MHz, $CDCl_3$) δ3.67 (s, 3 H), 2.90 (t, J=7.8 Hz, 2 H), 2.33 (t, J=7.3 Hz, 2 H), 1.80–1.60 (m, 4 H), 1.45–1.30 (m, 2 H).

C. O-benzylmethylpimelyl hydroxamate (6)

A suspension of O-benzyl hydroxylamine hydrochloride (43.3 g, 0.27 mol) and triethyl amine (80 mL, 0.57 mol) in $CH_2Cl_2$ (800 mL) under $N_2$ was prepared and added 52.2 g of methylpimeloyl chloride (8) (0.27 mol) from step B was added to the suspension over 15 min. After stirring overnight at room temperature, the mixture was washed with 0.5 N HCl (1×500 mL), 10% NaHCO3 (1×500 mL) and dried ($Na_2SO_4$). Purification by flash chromatography (silica gel; EtOAc/hexane (2:3, v/v) and EtOAc/hexane (1:1, v/v)) provided a light lime oil (68.2 g, 98%) identified as O-benzylmethylpimelyl hydroxamate (6); TLC ($SiO_2$, EtOAc/hexane (1:1, v/v) $R_f$=0.13; $^1$H NMR (360 MHz, $CDCl_3$) δ7.34 (br s, 5 H), 4.85 (br s, 2 H), 3.62 (s, 3 H), 2.26 (t, J=7.4 Hz, 2 H), 2.10–1.90 (m, 2 H), 1.70–1.50 (m, 4 H), 1.30–1.20 (m, 2 H); mass spectrum (ESI), m/z 280 ($MH^+$).

D. (L)-N-Boc-6-hydroxynorleucine (9)

To a solution of (L)-6-hydroxynorleucine (16) (12.0 g, 81.5 mmol) and triethylamine (11.4 mL, 81.8 mmol) in a tetrahydrofuran (THF)-water mixture (1:1, 420 mL) was added a solution of di-tert-butyl dicarbonate $(BOC)_2O$ (21.3 g, 97.6 mmol) in THF (30 mL). After stirring overnight at room temperature, the volume was reduced one-half under reduced pressure. To the mixture was added 1 N NaOH (100 mL) and was washed with EtOAc (3×100 mL). The aqueous layer was acidified to a pH 3 with citric acid (19.4 g, 101 mmol) and extracted with EtOAc (3×100 mL). The organic layer was dried ($Na_2SO_4$), filtered and the solvent removed under reduced pressure to provide a clear oil which crystallizes on standing in cooled storage to afford a white solid (18.7 g, 93%). The material was dissolved in EtOAc (350 mL) with heating (bath, 65° C.) and hexane (300 mL) was added gradually to the warm solution. The solution was allowed to stand overnight at room temperature and the white crystalline solids identified as (L)-N-Boc-6-hydroxynorleucine (9) were filtered and washed with EtOAc-hexane (1:1, 4×30 mL) (16.1 g, 80%): mp 113–115° C. (lit.[1] mp 112–113° C.).

E. (L)-N-Boc-6-hydroxynorleucine allyl ester (10)

A mixture of (L)-N-Boc-6-hydroxynorleucine (9) (28.5 g, 115 mmol), $NaHCO_3$ (15.5 g, 184 mmol), tricaprylymethylammonium chloride (a phase transfer catalyst), (10.1 g, 25 mmol), allyl bromide (13 mL, 150 mmol), $CH_2Cl_2$ (100 mL) and water (100 mL) was stirred vigorously at room temperature under $N_2$. After 8 days the mixture was filtered and purified by flash chromatography (silica gel; EtOAc/hexane (1:9, v/v) and EtOAc/hexane (2:3, v/v)) to provide a light lime oil (29.6 g, 89%) determined to be (L)-N-Boc-6-hydroxynorleucine allyl ester (10): TLC ($SiO_2$, EtOAc/hexane (1:1, v/v)) $R_f$=0.20; $^1$H NMR (300 MHz, $CDCl_3$) δ5.96–5.85 (m, 1 H), 5.38–5.24 (m, 2 H), 5.09 (br s,1 H), 4.72–4.58 (m, 2 H), 4.33 (br s, 1 H), 3.64 (t, J=6.3 Hz, 2 H), 1.96–1.20 (m, 15 H); mass spectrum (ESI), m/z 286 $(M-H)^-$.

To protect the carboxyl group of (L)-N-Boc-6-hydroxynorleucine (9), the ally ester was chosen. The ally ester was formed under mild conditions without the need to protect the alcohol. The allyl ester can be removed under mild conditions using a palladium(0)-catalyzed allyl transfer reaction in the presence of a methyl ester. This strategy was successful in the preparation of compound 2 described below. Other protecting strategies were considered, for e.g. phenacyl, 2-(trimethylsilyl) ethyl, and 2,6-dimethoxybenzyl esters. The protection of the alcohol group of 9 may be required with these other carboxyl protecting groups and the reagents (Zn/HoAc, DDQ) used in their cleavage may be unsuitable with other functionality present in compound 2.

F. (L)-N-Boc-6-bromonorleucine allyl ester (11a)

To a cooled ($^-$10–$^-$20° C. bath) solution of (L)-N-Boc-6-hydroxynorleucine allyl ester (10) from E above (40.6 g, 141 mmol) and carbon tetrabromide (51.6 g, 156 mmol) in anhydrous $CH_2Cl_2$ (400 mL) under $N_2$ was added triphenylphosphine $PPh_3$ (40.9 g, 156 mmol) over 25 min. The mixture was warmed to room temperature. After approximately 2 h, the mixture was concentrated under reduced pressure to provide a viscous oil. To the oil was added EtOAc/hexane (3:17 (v/v), 200 mL) and the precipitate filtered and washed with EtOAc/hexane (3:17 (v/v), 500 mL). The filtrate was concentrated under reduced pressure and purified by flash chromatography (silica gel; EtOAc/hexane (1:19, v/v) and EtOAc/hexane (1:4, v/v) to provide a light yellow oil identified as (L)-N-Boc-6-bromonorleucine allyl ester (11a) (41.8 g, 84%): TLC ($SiO_2$, EtOAc/hexane (1:1, v/v)) $R_f$=0.60; $^1$H NMR (360 MHz, $CDCl_3$) δ5.97–5.85 (m, 1 H), 5.36–5.24 (m, 2 H), 5.20 (br s,1 H), 4.70–4.58 (m, 2 H), 4.32 (br s, 1 H), 3.39 (t, J=6.6 Hz, 2 H), 1.95–1.80 (m, 3 H), 1.72–1.25 (m, 12 H); mass spectrum (ESI), m/z 350 ($MH^+$).

The above reaction can also be performed in tetrahydrofuran (THF) with the same results. As a third approach, N-bromo-succinimide can be used to generate 11a using dimethyl formamide (DMF) or methylene chloride ($CH_2Cl_2$). The yield was not determined but the product $R_f$ was identical to 11a (TLC ($SiO_2$, EtOAc/hexane (1:3, v/v)) $R_f$=0.36.

G. (L)-N-Boc-6-methanesulfonylnorleucine allyl ester (11b)

As an alternative approach, to a cooled (0° C. bath) solution of (L)-N-Boc-6-hydroxynorleucine allyl ester (10) from E above (80 mg, 0.28 mmol), triethyl amine (80 μL, 0.57 mmol), dimethyl amino pyridine (DMAP) (cat) in anhydrous $CH_2Cl_2$ (1 mL) under $N_2$ was added methane sulfonyl chloride (27 μL, 0.34 mmol). The contents were warmed (rt) and the mixture was concentrated under reduced pressure and purified by flash chromatography (silica gel; EtOAc/hexane, (1:19, v/v)) to provide a light yellow oil identified as (L)-N-Boc-6-methanesulfonylnorleucine allyl ester (11 b) (81 mg, 79%): TLC ($SiO_2$, EtOAc/hexane (1:1, v/v)) $R_f$=0.36; $^1$H NMR (360 MHz, $CDCl_3$) δ5.98–5.84 (m, 1 H), 5.38–5.24 (m, 2 H), 5.08–4.96 (m, 1 H), 4.70–4.58 (m, 2 H), 4.38–4.26 (m, 1 H), 4.21 (t, J=6.4 Hz, 2 H), 2.99 (s, 3 H), 1.95–1.35 (m, 15 H).

As a further alternative approach, the methanesulfonate can be prepared as a reactant for the coupling with hydroxamate 6. It was believed the methanesulfonate will decrease the overall reaction time and improve the yield of 5.

H. (L)-$N^6$-methylpimelyl-$N^6$-(benzyloxy)-$N^2$-Boc-lysine allyl ester (5)

A mixture of (L)-N-Boc-6-bromonorleucine allyl ester (11a) (19.5 g, 55.7 mmol), O-benzylmethylpimelyl hydroxamate (6) (20.0 g, 71.6 mmol), potassium iodide (KI) (5.0 g, 30.1 mmol) and potassium carbonate ($K_2CO_3$) (20.0 g, 144.7 mmol) in anhydrous acetone (125 mL) was heated at reflux under $N_2$ with vigorous stirring. After 6 days additional potassium iodide (1.0 g, 6.0 mmol) and potassium carbonate (4.0 g, 28.9 mmol) were added. After the 8th day still more potassium iodide (1.0 g, 6.0 mmol) and potassium carbonate (4.0 g, 28.9 mmol) were added to increase the yield. After 10 days, the mixture was cooled to room temperature, EtOAc (100 mL) was added and the solids filtered. The filtrate was concentrated under reduced pressure and the resultant lime colored oil was purified by flash chromatography (silica gel; EtOAc/hexane (1:4, v/v), EtOAc/hexane (2:3, v/v) and EtOAc/hexane, (3:2, v/v)) to provide a light yellow oil identified as (L)-$N^6$-methylpimelyl-$N^6$-(benzyloxy)-$N^2$-Boc-lysine allyl ester (5) (21.4 g, 70%): TLC ($SiO_2$, EtOAc/hexane (1:1, v/v)) $R_f$=0.36, O-alkylated products, $R_f$=0.56); $^1$H NMR (360 MHz, $CDCl_3$) δ7.45–7.30 (m, 6 H), 5.95–5.82 (m, 1 H), 5.35–5.20 (m, 2 H), 5.10–5.00 (m, 1 H), 4.79 (s, 2 H), 4.65–4.55 (m, 2 H), 4.32–4.20 (m, 1 H), 3.66 (s, 3 H), 3.70–3.55 (m, 2 H), 2.37 (t, J=7.5 Hz, 2 H), 2.29 (t, J=7.5 Hz, 2 H), 1.88–1.22 (m, 21 H); mass spectrum (ESI), m/z 549 ($MH^+$).

I. (L)-$N^6$-Methylpimelyl-$N^6$-(benzyloxy)-$N^2$-((L)-N-(2-(benzyloxy)benzoyl)serine)-lysine allyl ester (12)

Trifluoro acetic acid (TFA) (25 mL, 325 mmol) was added to (L)-$N^6$-methylpimelyl-$N^6$-(benzyloxy)-$N^2$-Boc-lysine allyl ester (5) (23.2 g, 42.3 mmol) in an ice bath. The mixture was warmed (45° C. bath). After approximately 2 h, excess TFA was removed under reduced pressure, $CH_2Cl_2$ (50 mL) was added and the pH was brought to approximately 8.0 (0–14 pH paper) with $Na_2CO_3$ (1.5 M, 70 mL). The organic layer was separated and the aqueous layer was extracted with $CH_2Cl_2$ (20 mL). The combined organic phase was dried over $K_2CO_3/Na_2SO_4$ (2:3, 50 g) and filtered to form a solid intermediate. The intermediate solids were rinsed with $CH_2Cl_2$ (50 mL) and the filtrate was added to (L)-N-(2-(benzyloxy)benzoyl)serine (4) (13.8 g, 43.8 mmol). To the resultant light yellow solution was added 2-ethoxy-1-ethoxycarbonyl-1,2-dihydroquinoline (EEDQ) (11.3 g, 45.7 mmol) at room temperature and the mixture was stirred overnight under $N_2$. The solvent was removed under reduced pressure, EtOAc (150 mL) was added and the mixture was washed with 0.25 M HCl (2×100 mL) and 10% $NaHCO_3$/saturated brine (4:1, 250 mL). After slow separation of the emulsion, the basic layer was back extracted with EtOAc (1×50 mL). The organic layers were combined and washed with saturated brine (2×150 mL) and dried ($Na_2SO_4$). A peach colored oil that remained was purified by flash chromatography (silica gel; EtOAc/hexane (2:1, v/v), EtOAc/hexane (4:1, v/v) and EtOAc/hexane (9:1, v/v)) to provide a light brown viscous oil identified as (L)-$N^6$-Methylpimelyl-$N^6$-(benzyloxy)-$N^2$-((L)-N-(2-(benzyloxy)benzoyl)serine)-lysine allyl ester (12) (24.8 g, 79%, purity 95% ($^1$H NMR), single spot by TLC): TLC ($SiO_2$, EtOAc/hexane (3:1, v/v)) $R_f$=0.20); $^1$H NMR (360 MHz, $CDCl_3$) δ8.73 (br d, J=6.8 Hz, 1 H), 8.20–8.14 (m, 1 H), 7.71–7.22 (m, 11 H), 7.10–7.00 (m, 2 H), 5.95–5.80 (m, 1 H), 5.35–5.18 (m, 4 H), 4.72 (s, 2 H), 4.70–4.45 (m, 4 H), 4.08–4.00 (m, 1 H), 3.65 (s, 3 H), 3.65–3.40 (m, 3 H), 3.15–3.05 (m, 1 H), 2.38–2.24 (m, 4 H), 1.90–1.48 (m, 8 H), 1.38–1.20 (m, 4 H); mass spectrum (ESI), m/z 746 ($MH^+$).

J. (L)-$N^6$-Methylpimelyl-$N^6$-(benzyloxy)-$N^2$-((S)-2-(2-benzyloxy) phenyl)-2-oxazoline-4-carbonyl)-lysine allyl ester (13)

Thionyl chloride ($SOCl_2$) (19 mL, 260 mmol) was gradually added to a cooled (⁻30° C. bath) solution of the lysine allyl ester (12) of Step 1 (24.0 g, 32.2 mmol) in anhydrous tetrahydrofuran (THF) (80 mL). After mixing, the reaction was placed in a freezer (⁻20° C.) overnight. The chilled mixture was added dropwise to 1.2 M $Na_2CO_3$ (500 mL) (final pH≅8)) and extracted with EtOAc (2×150 mL). The combined organic materials were washed with saturated brine (1×150 mL) and dried ($Na_2SO_4$). A golden colored oil was then purified by flash chromatography (silica gel; i-PrOH/hexane (1:9, v/v), EtOAc/hexane (2:1, v/v)) to provide a light brown viscous oil identified as (L)-$N^6$-Methylpimelyl-$N^6$-(benzyloxy)-$N^2$-((S)-2-(2-benzyloxy) phenyl)-2-oxazoline-4-carbonyl)-lysine allyl ester (13) (17.1 g, 73%, purity≅95% ($^1$H NMR): TLC ($SiO_2$, EtOAc/hexane (3:1, v/v)) $R_f$=0.40); $^1$H NMR (360 MHz, $CDCl_3$) δ7.83–7.78 (m, 1 H), 7.53–7.25 (m, 11 H), 7.20–7.12 (m, 1 H), 7.05–6.97 (m, 2 H), 5.95–5.80 (m, 1 H), 5.35–5.18 (m, 4 H), 4.91 (dd, J=10.3, 8.4 Hz, 1 H), 4.71 (s, 2 H), 4.65–4.47 (m, 5 H), 3.65 (s, 3 H), 3.52–3.40 (m, 2 H), 2.33–2.25 (m, 4 H), 1.80–1.15 (m, 12 H); mass spectrum (ESI), m/z 728 (MH$^+$), 726 (M–H)$^-$.

K. Compound 14a

To the solution of oxazoline-lysine allyl ester (13) from Step J (8.1 g, 11.1 mmol) in anhydrous $CH_2Cl_2$ (50 mL) was added morpholine (1.1 mL, 12.5 mmol) and tetrakis (triphenylphosphine) palladium (Pd(PPh$_3$)$_4$) (0.1 g, 0.09 mmol) under $N_2$ at room temperature. After 1 hour, the solvent was removed under reduced pressure, EtOAc (100 mL) was added to the mixture and the organics were washed with 0.25 M HCl (1×60 mL), sat. brine (3×50 mL), dried ($Na_2SO_4$), filtered and the solvent was removed under reduced pressure. The light brown oil was subject to co-evaporation with toluene (3×10 mL) and dried under vacuum for approximately 1 hour to provide acid 2 as a tan glass [mass spectrum (ESI), m/z 688 (MH$^+$), 686 (M–H)$^-$]. To a solution of acid 2, (L)-N$^\alpha$-((S)-3-hydroxybutyryl)-α-amino-N-(benzyloxy) caprolactam (3a) or (3b) (3.5 g, 10.9 mmol) and PPh$_3$ (5.6 g, 21.4 mmol) in anhydrous THF (70 mL), cooled (0° C. bath) under $N_2$ was gradually added deithyl azodicarboxylate (DEAD) (3.4 mL, 21.6 mmol). The cooling bath was removed and the contents stirred overnight. The solvent was removed under reduced pressure and the golden oil shown in FIG. 5 as 14a was purified by two sequential flash chromatographies: chromatography 1 (silica gel; i-PrOH/hexane (3:7, v/v), i-PrOH/hexane (2:3, v/v)), chromatography 2 (silica gel; CH$_2$CL2/EtOAc (3:17, v/v), EtOAc) to provide a light brown glass (5.3 g, 49%, purity 90–95% ($^1$H NMR)): TLC (SiO$_2$, MeOH/EtOAc, (1:32,v/v)) R$_f$=0.30); $^1$H NMR (360 MHz, CDCl$_3$) δ7.80 (dd, J=8.0, 1.7 Hz, 1 H), 7.49 (br d, J=7.0 Hz, 2 H), 7.45–7.24 (m, 14 H), 7.19 (brd, J=8.0Hz, 1 H), 7.04–6.96 (m, 3 H), 5.37–5.18 (m, 3 H), 5.02–4.85 (m, 3 H, includes AB quartet 4.98 (J=8.0 Hz), 4.88 (J=8.0 Hz)), 4.71 (s, 2 H), 4.63–4.52 (m, 2 H), 4.50–4.41 (m, 2 H), 3.68–3.40 (m, 4 H), 3.65 (s, 3 H), 2.55 (dd, J=14.5, 6.8 Hz, 1 H), 2.44 (dd, J=14.5, 5.9 Hz, 1 H), 2.36–2.25 (m, 4 H), 2.02–1.82 (m, 2 H), 1.80–1.15 (m, 16 H), 1.30 (d, J=6.3 Hz, 3 H); mass spectrum (ESI), m/z 991 (MH$^+$), 989 (M–H)$^-$.

It was found by TLC that Acid 2 should be used immediately as some decomposition occurred when stored overnight at low temperature (4° C.).

Some alternatives to the Mitsunobu coupling described above include:

1. Carboxyl group activation using mixed anhydrides, N-acylimidazoles and activated esters (e.g. BOP).
2. Hydroxy group activation using dicyclohexylcarbodiimide (DCC).

L. Compound 14b

Was prepared in a similar way as 14a with a similar yield except (L)-N$^\alpha$-((R)-3-hydroxybutyryl)-α-amino-N-(benzyloxy) caprolactam (3b) was used: TLC (SiO$_2$, MeOH/EtOAc (1:32, v/v)) R$_f$=0.30); $^1$H NMR (360 MHz, CDCl$_3$) δ$^1$H NMR (360 MHz, CDCl$_3$) δ7.80 (dd, J=8.0, 1.7 Hz, 1 H), 7.50 (br d, J=7.1 Hz, 2 H), 7.44–7.26 (m, 14 H), 7.18 (br s, 1 H), 7.04–6.96 (m, 3 H), 5.35–5.18 (m, 3 H), 5.03–4.85 (m, 3 H, includes AB quartet 4.92 (J=10.5 Hz), 4.82 (J=10.5 Hz)), 4.70 (s, 2 H), 4.63–4.55 (m, 2 H), 4.48–4.39 (m, 2 H), 3.67–3.58 (m, 1 H), 3.65 (s, 3 H), 3.56–3.41 (m, 3 H), 2.57 (dd, J=14.5, 6.9 Hz, 1 H), 2.40 (dd, J=14.5, 6.2 Hz, 1 H), 2.36–2.24 (m, 4 H), 2.02–1.95 (m, 1 H), 1.95–1.82 (m, 1 H), 1.82–1.18 (m, 16 H), 1.33 (d, J=6.3 Hz, 3 H); mass spectrum (ESI), m/z 990 (MH$^+$), 988 (M–H)$^-$.

M. Exochelin 772SM(R) (1a)

The material isolated in Step K or L (5.5g, 5.6 mmol) above was mixed with MeOH (350 mL) in a round bottom flask and degassed with $N_2$. 10% Pd/C (0.5 g) was added and a balloon filled with $H_2$ was attached to the flask. After stirring overnight at room temperature, the 10% Pd/C was allowed to settle and the solution was filtered through a 0.45 μm syringe filter. The remaining solids were washed with MeOH (20 mL) and filtered likewise. The solvent was removed under reduced pressure and co-evaporated with $CH_2Cl_2$ to provide an off-white flaky solid (3.8 g, 95%, purity 95%, Fe content≅1.9%):. NMR analysis indicated that this material was the desired exochelin shown as formula 1a. TLC (SiO$_2$, MeOH/CH$_2$Cl$_2$ (1:19, v/v)) R$_f$=0.14–0.24); $^1$H NMR (360 MHz, CDCl$_3$) δ7.63 (d (with further small coupling), J=8.0 Hz, 1 H), 7.35 (t (with further small coupling), J=8.3 Hz, 1 H), 6.95 (d, J=8.3 Hz, 1 H), 7.4–6.9 (m, 2 H), 6.85 (t (with further small coupling), J=8.0 Hz, 1 H), 5.28–5.15 (m, 1 H), 4.90 (t, J=9.5 Hz, 1 H), 4.65–4.49 (m (includes doublet 4.60, J=9.5 Hz), 3 H), 4.45 (br dd, J=10.2, 6.3 Hz, 1 H), 3.80–3.62 (m, 2 H), 3.59 (s, 3 H), 3.55–3.35 (m, 2 H), 2.50 (d, J=5.7 Hz, 2 H), 2.48–2.10 (m (includes triplet, 2.23 (J=7.3 Hz)), 4 H), 1.98–1.42 (m, 13 H), 1.42–1.20 (m (includes doublet, 1.28 (J=6.1 Hz)), 8 H); mass spectrum (ESI), m/z 720 (MH$^+$), 718 (M–H)$^-$.

Compound 1b

Was prepared from 14b in a similar manner as the preparation of 1a with a similar yield as an off-white flaky solid: TLC (SiO$_2$, MeOH/EtOAc (1:32, v/v)) R$_f$=0.0–0.13); $^1$H NMR (360 MHz, CDCl$_3$) δ7.69 (d (with further small coupling), J=8.0 Hz, 1 H), 7.42 (t (with further small coupling), J=8.3 Hz, 1 H), 7.20–7.0 (br s, 2 H), 7.02 (d, J=8.6 Hz, 1 H), 6.91 (t (with further small coupling), J=8.0 Hz, 1 H), 5.35–5.25 (m, 1 H), 4.95 (t, J=9.5 Hz, 1 H), 4.65 (br d, J=9.5 Hz, 2 H), 4.58–4.48 (m, 2 H), 3.82–3.50 (m (includes singlet 3.65), 7 H), 2.60–2.20 (m (includes triplet, 2.31 (J=7.4 Hz)), 6 H), 2.08–1.20 (m, includes doublet, 1.35 (J=6.6 Hz)), 21 H); mass spectrum (ESI), m/z 720 (MH$^+$), 718 (M–H)$^-$.

Functional Studies of Synthetic Desferri-Exochelins

The exochelins prepared in accordance with the above procedure were tested to show that their performance in medical procedures was equivalent to previously shown performance of biologically derived exochelins.

I. Synthetic Desferri-Exochelin 772SM(R)

A. Capacity to Chelate Iron

To determine if the synthetic desferri-Exochelin 772SM (R) could chelate iron, as does the native form, the Exochelin was dissolved in 0.1% TFA containing ferric ammonium citrate at a 10-fold molar excess of iron to Exochelin. The solution was then loaded on a Bondapak Phenyl 125 Å 10 μm (3.9×300 mm) HPLC column and the Exochelin was subjected to reverse-phase HPLC (High Pressure Liquid Chromatography) on a Rainin (Woburn, Mass.) HPXL system. The Exochelin was eluted with a 0–100% gradient of a buffer consisting of 0.1% TFA and 50% acetonitrile at a flow rate of 1 ml/min. The ferri-exochelins were monitored at 220-nm and 450-nm absorbance. The mass of ferri-exochelin was assayed by measuring the area under the peak at 450-nm and applying a conversion factor derived from assaying known amounts of ferri-exochelin 772SM(R).

In the absence of ferric ammonium citrate, only a small amount of ferri-exochelin was eluted from the HPLC column, amounting to 1.08% of the Exochelin added. In the presence of ferric ammonium citrate, 100% of the exochelin eluted from the column in the ferri form.

Thus, synthetic desferri-exochelin 772SM(R) rapidly chelates ferric iron in solution.

B. Elution Profile on Reverse-Phase HPLC

Synthetic Exochelin 772SM(R) and native Exochelin 772SM(R) were separately diluted in water containing 0.1%

TFA and excess ferric ammonium citrate and individually loaded on a phenyl column as described above. The Exochelins were eluted with a 0–100% gradient of a buffer consisting of 0.1% TFA and 50% acetonitrile at a flow rate of 1 ml/min on a Rainin (Woburn, Mass.) HPXL system. The Exochelins were identified by their 450-nm absorbance.

Synthetic Exochelin 772SM(R) and native Exochelin 772SM(R) eluted at precisely the same concentration of acetonitrile on reverse-phase HPLC. Further, when the two Exochelins were mixed together and subjected to reverse-phase HPLC, they eluted as a single sharp peak and the mass of Exochelin in the peak—assayed by measuring the area under the 450 nm absorbance peak and applying a conversion factor derived from measurement of known amounts of Exochelin 772SM(R)—was equal to the sum of their individual masses.

Thus, synthetic desferri-Exochelin 772SM(R) has the same elution profile on reverse-phase HPLC as native Exochelin 772SM(R).

C. Capacity to Remove Iron from a Different Exochelin Species

To assess the affinity of the synthetic desferri-Exochelin 772SM(R) for iron, its capacity to remove iron from a different Exochelin species, ferri-Exochelin 758SM, was evaluated. The capacity of synthetic and native desferri-Exochelin 772SM(R) to remove iron from ferri-Exochelin 758SM was also evaluated and compared. Either native or synthetic desferri-Exochelin 772SM(R) were independently mixed with ferri-Exochelin 758SM. The amount of iron acquired in 1 hour by the desferri-Exochelins was assayed by subjecting the Exochelin to reverse-phase HPLC on a phenyl column, as described above, and the area under the 450 nm absorbance peak was measured. The amount of iron-Exochelin was then calculated using a conversion factor derived from assaying known amounts of ferri-Exochelin 772SM(R).

In a first experiment, 26.1 $\mu$g of 1. 1% iron-saturated synthetic Exochelin 772SM(R) was mixed with 17.8 $\mu$g of 100% iron-saturated native Exochelin 758SM. Assuming the two exochelins have comparable affinities for iron, the calculated iron-saturation at equilibrium is 41.2%. At 1 h, the synthetic Exochelin 772SM(R) was 33.5% iron-saturated, i.e. it had reached 81.3% of the theoretical iron-saturation at equilibrium (Table 1, Experiment Ia).

The process was repeated by mixing 15.1 $\mu$g of 2.8% iron-saturated native Exochelin 772SM(R) with 16.9 $\mu$g of 100% iron-saturated native Exochelin 758SM. Assuming the two exochelins have comparable affinities for iron, the calculated iron-saturation at equilibrium is 54.1%. At 1 h, the native Exochelin 772SM(R) was 46.4% iron-saturated, i.e. it had reached 85.8% of the theoretical iron-saturation at equilibrium (Table 1, Experiment Ib).

In a second experiment, 17.3 $\mu$g of 1.1% iron-saturated synthetic Exochelin 772SM(R) was mixed with 19.8 $\mu$g of 100% iron-saturated native Exochelin 758SM. Assuming the two exochelins have comparable affinities for iron, the calculated iron-saturation at equilibrium is 53.9%. At 1 h, the synthetic Exochelin 772SM(R) was 48.6% iron-saturated, i.e. it had reached 90.2% of the theoretical iron-saturation at equilibrium (Table 1, Experiment IIa).

Using 15.8 $\mu$g of 2.8% iron-saturated native Exochelin 772SM(R) the process was repeated using 19.1 $\mu$g of 100% iron-saturated native Exochelin 758SM. Assuming the two exochelins have comparable affinities for iron, the calculated iron-saturation at equilibrium is 55.9%. At 1 h, the native Exochelin 772SM(R) was 45.6% iron-saturated, i.e. it had reached 81.6% of the theoretical iron-saturation at equilibrium (Table 1, Experiment IIb).

These experiments demonstrate a) that the synthetic desferri-Exochelin 772SM(R) has a very high affinity for iron since it is able to remove iron rapidly from an iron-binding molecule known to have a high affinity for iron, and b) that the synthetic and native desferri-Exochelin 772SM (R) have comparable capacities to remove iron from a high affinity iron-binding molecule.

TABLE 1

Capacity of Synthetic and Native Desferri-Exochelin 772SM(R) to Remove Iron from a Different Exochelin Species (Ferri-Exochelin 758SM)

| | Mass | % Iron-Saturation | | % of Calculated Iron-Saturation at Equilibrium | |
|---|---|---|---|---|---|
| | ($\mu$g) | 0 h | 1 h | 0 h | 1 h |
| Experiment I | | | | | |
| a) Native 758SM | 17.8 | 100 | 49.4 | — | — |
| Synthetic 772SM(R) | 26.1 | 1.1 | 33.5 | 2.7% | 81.3% |
| b) Native 758SM | 16.9 | 100 | 63.9 | — | — |
| Native 772SM(R) | 15.1 | 2.8 | 46.4 | 6.8% | 85.8% |
| Experiment II | | | | | |
| a) Native 758SM | 19.8 | 100 | 61.6 | — | — |
| Synthetic 772SM(R) | 17.3 | 1.1 | 48.6 | 2.0% | 90.2% |
| b) Native 758SM | 19.1 | 100 | 66.5 | — | — |
| Native 772SM(R) | 15.8 | 2.8 | 45.6 | 5.0% | 81.6% |

II. Synthetic Desferri-Exochelin 772SM(S)

The test as set forth above for the (R) form were repeated for the (S) form.

A. Capacity to Chelate Iron

The capacity of synthetic Exochelin 772SM(S) to chelate iron from a solution containing a 10-fold molar excess of ferric iron (ferric ammonium citrate) was assayed as described above. In the absence of ferric ammonium citrate, only 1.03% of the exochelin contained iron. In the presence of ferric ammonium citrate, the exochelin was fully saturated with iron.

Thus, synthetic desferri-Exochelin 772SM(S) rapidly chelates iron in solution.

B. Elution Profile on Reverse-Phase HPLC

Synthetic Exochelin 772SM(S) and native Exochelin 772SM(R) were diluted in water containing 0.1% TFA and a 10-fold molar excess of ferric iron (ferric ammonium citrate) and individually subjected to reverse phase HPLC as described above.

Synthetic Exochelin 772SM(S) eluted approximately 1 minute later in the acetonitrile gradient than native Exochelin 772SM(R).

Thus, as a consequence of the steric change at one asymmetric carbon, the synthetic Exochelin 772SM(S) has a slightly different elution profile than the native Exochelin 772SM(R).

C. Capacity to Remove Iron from a Different Exochelin Species

To assess the affinity of the synthetic desferri-Exochelin 772SM(S) for iron, its capacity to remove iron from a different exochelin species, ferri-Exochelin 758SM. was evaluated. The capacity of synthetic desferri-Exochelin 772SM(S) and native desferri-Exochelin 772SM(R) to remove iron from ferri-Exochelin 758SM was also evaluated and compared. Either synthetic desferri-Exochelin 772SM (S) or native desferri-Exochelin 772SM(R) was mixed with ferri-Exochelin 758SM. The amount of iron acquired by the desferri-exochelins after 1 hour was assayed by subjecting the molecule to reverse-phase HPLC on a phenyl column, as described above, and the area under the 450 nm absorbance peak was measured. The amount of iron-exochelin was then calculated using a conversion factor derived from assaying known amounts of ferri-Exochelin 772SM(R) and ferri-Exochelin 772SM(S).

Specifically, 17.4 μg of 1.0% iron-saturated synthetic Exochelin 772SM(S) was mixed with 13.5 μg of 100% iron-saturated native Exochelin 758SM. Assuming the two exochelins have comparable affinities for iron, the calculated iron-saturation at equilibrium is 44.3%. At 1 h, the synthetic Exochelin 772SM(S) was 39.7% iron-saturated, i.e. it had reached 89.6% of the theoretical iron-saturation at equilibrium (Table 2, Experiment 1).

In Experiment 2, 13.0 μg of 2.8% iron-saturated native Exochelin 772SM(R) was mixed with 13.3 μg of 100% iron-saturated native Exochelin 758SM. Assuming the two exochelins have comparable affinities for iron, the calculated iron-saturation at equilibrium is 52.1%. At 1 h, the native Exochelin 772SM(R) was 46.2% iron-saturated, i.e. it had reached 88.7% of the theoretical iron-saturation at equilibrium (Table 2, Experiment 2).

As a third demonstration, the capacity of synthetic desferri-Exochelin 772SM(S) was compared with synthetic desferri-Exochelin 772SM(R) to remove iron from a different exochelin species.

15.6 μg of 1.1% iron-saturated synthetic Exochelin 772SM(R) was mixed with 13.6 μg of 100% iron-saturated native Exochelin 758SM. Assuming the two exochelins have comparable affinities for iron, the calculated iron-saturation at equilibrium is 47.3%. At 1 h, the synthetic Exochelin 772SM(R) was 42.9% iron-saturated, i.e. it had reached 90.7% of the theoretical iron-saturation at equilibrium (Table 2, Experiment 3).

These experiments demonstrate a) that the synthetic desferri-Exochelin 772SM(S) has a very high affinity for iron since it is able to remove iron rapidly from a high affinity iron-binding molecule; b) that synthetic desferri-Exochelin 772SM(S) and native desferri-Exochelin 772SM(R) have comparable capacities to remove iron from a high affinity iron-binding molecule; and c) that the synthetic stereoisomers desferri-Exochelin 772SM(S) and 772SM(R) have comparable affinity for iron.

TABLE 2

Capacity of Synthetic Desferri-Exochelin 772SM(S), Native Desferri-Exochelin 772SM(R), and Synthetic Desferri-Exochelin 772SM(R) to Remove Iron from a Different Exochelin Species (Ferri-Exochelin 758SM)

|  | Mass | % Iron-Saturation | | % of Calculated Iron-Saturation at Equilibrium | |
| --- | --- | --- | --- | --- | --- |
|  | (μg) | 0 hour | 1 hour | 0 hour | 1 hour |
| Experiment 1 | | | | | |
| a) Native 758SM | 13.5 | 100 | 54.1 | — | — |
| b) Synthetic 772SM(S) | 17.4 | 1.0 | 39.7 | 2.3% | 89.6% |
| Experiment 2 | | | | | |
| a) Native 758SM | 13.3 | 100 | 61.7 | — | — |
| b) Native 772SM(R) | 13.0 | 2.8 | 46.2 | 5.4% | 88.7% |
| Experiment 3 | | | | | |
| a) Native 758SM | 13.6 | 100 | 55.9 | — | — |
| b) Synthetic 772SM(R) | 15.6 | 1.1 | 42.9 | 2.3% | 90.7% |

III. Synthetic Desferri-Exochelin 772SM(R) vs. 772SM(S)

To further assess the relative affinities of the stereoisomers desferri-Exochelins 772SM(R) and 772SM(S) for iron, their capacity to remove iron from a different exochelin species in the same vial were compared.

In the experiment, 15.6 μg of 1.1% iron-saturated synthetic Exochelin 772SM(R) and 17.4 μg of 1.0% iron-saturated synthetic Exochelin 772SM(S) was mixed with 13.5 μg of 100% iron-saturated native Exochelin 758SM. Assuming the three exochelins have comparable affinities for iron, the calculated iron-saturation at equilibrium is 29.9%. At 1 h, the synthetic Exochelin 772SM(R) was 28.2% iron-saturated, i.e. it had reached 94.3% of the theoretical iron-saturation at equilibrium and Exochelin 772SM(S) was 25.9% iron-saturated, i.e. it had reached 86.6% of the theoretical iron-saturation at equilibrium (Table 3).

Thus, the two stereoisomers have nearly the same affinity for iron.

TABLE 3

Capacity of Synthetic Desferri-Exochelin 772SM(S) and Synthetic Desferri-Exochelin 772SM(R) to Remove Iron from a Different Exochelin Species (Ferri-Exochelin 758SM) in the Same Vial

|  | Mass | % Iron-Saturation | | % of Calculated Iron-Saturation at Equilibrium | |
| --- | --- | --- | --- | --- | --- |
|  | (μg) | 0 hour | 1 hour | 0 hour | 1 hour |
| Native 758SM | 13.5 | 100 | 40.0 | — | — |
| Synthetic 772SM(R) | 15.6 | 1.1 | 28.2 | 3.7% | 94.3% |
| Synthetic 772SM(S) | 17.4 | 1.0 | 25.9 | 3.3% | 86.6% |

IV. Capacity of Native Desferri-Exochelin 772SM(R), Synthetic Desferri-Exochelin 772SM(R), and Synthetic Desferri-Exochelin 772SM(S) to Remove Iron from 40% Iron-Saturated Transferrin, Holo-Transferrin, and Apotransferrin A. 40% Iron-Saturated Human Transferrin To assess the capacity of the 3 different desferri-Exochelins to remove iron from 40% iron-saturated human transferrin, each of them was incubated for 1, 3, and 24 hours with 40% iron-saturated transferrin such that the ratio of $Fe^{3+}$:desferri-Exochelin equaled 10:1. The incubation was carried out in PBS, pH 7.4. Afterwards, the Exochelin and transferrin were separated from each other by centrifugation through a 10,000 dalton cut-off filter. The transferrin (mass 76,000 daltons) was completely excluded by this filter whereas 85% of the Exochelin (mass<1,000) was recovered in the filtrate. To determine the total amount of exochelin recovered, the exochelin in the filtrate was saturated with a 20:1 molar excess of ferric ammonium citrate and subjected to reverse-phase HPLC as described above. To determine the amount of iron-saturated Exochelin in the filtrate at each time point, the filtrate was subjected to reverse-phase HPLC without the addition of iron. The % iron-saturation was calculated as follows:

$$\frac{\text{Iron-Saturated Exochelin with addition of FAC (}\mu\text{g)}}{\text{Iron-saturated Exochelin without addition of FAC (}\mu\text{g)}} \times 100$$

Each of the desferri-exochelins removed iron from 40% iron-saturated transferrin in a time-dependent fashion (Table 4). After 24 hours, native desferri-exochelin 772SM(R) was 34.0% iron-saturated, synthetic desferri-exochelin 772SM(R) was 39.2% iron-saturated, and synthetic desferri-exochelin 772SM(S) was 35.3% iron-saturated. Thus, all three desferri-exochelins efficiently removed iron from 40% saturated iron-transferrin, and their capacity to do so was roughly comparable to each other.

TABLE 4

Capacity of Synthetic and Native Desferri-Exochelin 772SM(R) and Synthetic Desferri-Exochelin 772SM(S) to Remove Iron from 40% Iron-Saturated Human Transferrin

| | Mass (μg) | Iron-Saturation | | | |
|---|---|---|---|---|---|
| | | 0 h | 1 h | 3 h | 24 h |
| Native Desferri-Exochelin 772SM(R) | 8 | 2.8% | 9.3% | 13.8% | 34.0% |
| Synthetic Desferri-Exochelin 772SM(R) | 12.8 | 1.1% | 6.8% | 12.8% | 39.2% |
| Synthetic Desferri-Exochelin 772SM(S) | 12.8 | 1.0% | 14.2% | 13.8% | 35.3% |

B. Holo-Transferrin (92% Iron-Saturated Human Transferrin)

To assess the capacity of the 3 different desferri-Exochelins to remove iron from holo-transferrin (92% iron-saturated human transferring, each of them was incubated for 1, 3, and 24 h with 92% iron-saturated transferrin such that the ratio of $Fe^{3+}$: desferri-Exochelin equaled 10:1, as in the aforementioned study with 40% iron-saturated transferrin. The % iron-saturation of the Exochelins was assayed as above.

Each of the desferri-Exochelins removed iron from 92% iron-saturated transferrin in a time-dependent fashion (Table 5). By 24 h, native desferri-exochelin 772SM(R) was 54.1% iron-saturated, synthetic desferri-exochelin 772SM(R) was 60.0% iron-saturated, and synthetic desferri-exochelin 772SM(S) was 47.2% iron-saturated. Thus, all three desferri-exochelins efficiently removed iron from 92% saturated iron-transferrin, and their capacity to do so was roughly comparable to each other.

TABLE 5

Capacity of Synthetic and Native Desferri-Exochelin 772SM(R) and Synthetic Desferri-Exochelin 772SM(S) to Remove Iron from 92% Iron-Saturated Human Transferrin

| | Mass (μg) | Iron-Saturation | | | |
|---|---|---|---|---|---|
| | | 0 h | 1 h | 3 h | 24 h |
| Native Desferri-Exochelin 772SM(R) | 10.1 | 2.8% | 11.6% | 19.0% | 54.1% |
| Synthetic Desferri-Exochelin 772SM(R) | 12.1 | 1.1% | 13.6% | 31.5% | 60.0% |
| Synthetic Desferri-Exochelin 772SM(S) | 13.7 | 1.0% | 18.1% | 15.5% | 47.2% |

C. Apotransferrin (<0.7% Iron-Saturated Human Transferrin)

As a control, the three desferri-exochelins were incubated for 3 h and 24 h with human apotransferrin (<0.7% iron-saturated) at a concentration of 38 mg/ml, the same concentration of protein as in the study utilizing 92% iron-saturated transferrin in B above. None of the desferri-exochelins acquired appreciable amounts of iron (Table 6).

TABLE 6

Capacity of Synthetic and Native Desferri-Exochelin 772SM(R) and Synthetic Desferri-Exochelin 772SM(S) to Remove Iron from Human Apotransferrin (<0.7% Iron-Saturated)

| | Mass (μg) | Iron-Saturation | | |
|---|---|---|---|---|
| | | 0 h | 3 h | 24 h |
| Native Desferri-Exochelin 772SM(R) | 10.1 | 2.8% | 9.3% | 6.8% |
| Synthetic Desferri-Exochelin 772SM(R) | 12.1 | 1.1% | 5.2% | 6.9% |
| Synthetic Desferri-Exochelin 772SM(S) | 13.7 | 1.0% | 5.0% | 4.1% |

Based on the above, those skilled in the art would recognize that if pimelic acid 15 were replaced by acids of the family as shown by formula B below, various different Exochelins, listed in Table 7 would result. Table 7 below lists representative acids and the resultant Exochelin.

$$CO_2H-(CH_2)_n-CO_2H \qquad B$$

TABLE 7

Alternate Acid Reactants & Resultant Exochelins

Serine Saturated Series

| B | n | Exochelin (mw) |
|---|---|---|
| Azelaic Acid | n = 7 | 800 SM(R) or SM(S) |
| Suberic Acid | n = 6 | 786 SM(R) or SM(S) |
| Pimelic Acid | n = 5 | 772 Sm(R) or SM(S) |
| Adipic Acid | n = 4 | 758 SM(R) or SM(S) |
| Glutaric Acid | n = 3 | 744 SM(R) or SM(S) |
| Succinic Acid | n = 2 | 730 SM(R) or SM(S) |
| Malonic Acid | n = 1 | 716 SM(R) or SM(S) |

Theonine Saturated Series

| B | n | C(mw) |
|---|---|---|
| Azelaic Acid | n = 7 | 814 TM(R) or TM(S) |
| Suberic Acid | n = 6 | 800 TM(R) or TM(S) |
| Pimelic Acid | n = 5 | 786 Tm(R) or TM(S) |
| Adipic Acid | n = 4 | 772 TM(R) or TM(S) |
| Glutaric Acid | n = 3 | 758 TM(R) or TM(S) |
| Succinic Acid | n = 2 | 744 TM(R) or TM(S) |
| Malonic Acid | n = 1 | 730 TM(R) or TM(S) |

Also if pimelilc acid 15 were replaced by the acids as shown by D below, the Exochelin listed in Table 8 would result. The left columns identify alternative acid formulations.

$$CO_2H-(CH_2)_xCH=(CH_2)_y-CO_2H \qquad D$$

TABLE 8

Alternative Acid Reactants & Resultant Exochelins

Serine Unsaturated Series

| D | | | | Acid | Exochelin |
|---|---|---|---|---|---|
| x | y | X | Y | | |
| 1 | 0 | 0 | 1 | trans-glutacorric acid | 742SM(R) or (S) |
| | | 1 | 1 | trans-3-hexenedioric acid | 756SM(R) or (S) |
| 0 | 2 | 2 | 0 | trans-2-hexenedioric acid | 756SM(R) or (S) |
| 1 | 2 | 2 | 1 | trans-3-heptenediorc acid | 770SM(R) or (S) |
| 0 | 3 | 3 | 0 | trans-2-hexenedioric acid | 770SM(R) or (S) |
| 0 | 4 | 4 | 0 | trans-2-octenedioric acid | 784SM(R) or (S) |
| 1 | 3 | 3 | 1 | trans-3-octenedioric acid | 784SM(R) or (S) |
| | | 2 | 2 | trans-4-octenedioric acid | 784SM(R) or (S) |
| 0 | 5 | 5 | 0 | trans-2-octenedioric acid | 798SM(R) or (S) |
| 1 | 4 | 4 | 1 | trans-3-nonenedioric acid | 798SM(R) or (S) |
| 2 | 3 | 3 | 2 | trans-4-nonenedioric acid | 798SM(R) or (S) |

TABLE 8-continued

Alternative Acid Reactants & Resultant Exochelins

Threonine Unsaturated Series

D

| x | y | X | Y | Acid | Exochelin |
|---|---|---|---|---|---|
| 1 | 0 | 0 | 1 | trans-glutacorric acid | 752TM(R) or TM(S) |
|   | 1 | 1 |   | trans-3-hexenedioric acid | 770TM(R) or TM(S) |
| 0 | 2 | 2 | 0 | trans-2-hexenedioric acid | 770TM(R) or TM(S) |
| 1 | 2 | 2 | 1 | trans-3-heptenedioric acid | 784TM(R) or TM(S) |
| 0 | 3 | 3 | 0 | trans-2-hexenedioric acid | 784TM(R) or TM(S) |
| 0 | 4 | 4 | 0 | trans-2-octenedioric acid | 798TM(R) or TM(S) |
| 1 | 3 | 3 | 1 | trans-3-octenedioric acid | 798TM(R) or TM(S) |
|   | 2 | 2 |   | trans-4-octenedioric acid | 798TM(R) or TM(S) |
| 0 | 5 | 5 | 0 | trans-2-octenedioric acid | 812TM(R) or TM(S) |
| 1 | 4 | 4 | 1 | trans-3-nonenedioric acid | 812TM(R) or TM(S) |
| 2 | 3 | 3 | 2 | trans-4-nonenedioric acid | 812TM(R) or TM(S) |

Based on the above one can readily select alternate saturated or unsaturated acids for producing different Exochilins.

Although the present invention has been described in considerable detail with reference to certain preferred versions and uses thereof, other versions and uses are possible. Therefore, the spirit and scope of the appended claims should not be limited to the description of the preferred versions contained herein.

What is claimed is:

1. A method to synthesize an Exochelin comprising the steps of:

a) reacting a mixture of an acid having a formula of

where A is $(CH_2)_n$ or $(CH_2)_x CH=CH(CH_2)_y$, n is from 1 to 7, and x and y are from 0 to 5, with dimethyl pimelate, hydrochloric acid, methanol and di-n-butyl ether to produce a methylated acid, b) mixing the methylated acid with thionyl chloride and dimethyl formamide to replace an OH group thereon with chlorine c) adding the product from b) to a suspension of O-benzyl hydroxylamine hydrochloride and triethyl amine in $CH_2Cl_2$ to produce an O-benzylmethyl hydroxamate;

d) to a solution of (L)-6-hydroxynorleucine and triethylamine in a tetrahydrofuran (THF)-water adding a solution of di-tert-butyl dicarbonate in THF, e) separating an aqueous layer and acidifying the aqueous layer to pH 3 with citric acid and extracting that layer with EtOAc, f) drying and purifying the EtOAc layer to produce (L)-N-Boc-6-hydroxynorleucine, g) reacting the (L)-N-Boc-6-hydroxynorleucine with allyl bromide to produce (L)-N-Boc-6-hydroxynorleucine allyl ester, h) adding carbon tetrabromide in anhydrous $CH_2Cl_2$ and triphenylphosphine to the (L)-N-Boc-6-hydroxynorleucine allyl ester to provide a viscous oil, i) adding the viscous oil to EtOAc/hexane to produce (L)-N-Boc-6-bromonorleucine allyl ester j) mixing the (L)-N-Boc-6-bromonorleucine allyl ester, with the O-benzylmethyl hydroxamate, potassium iodide (KI) and potassium carbonate in anhydrous acetone to produce an (L)-$N^6$-methyl-$N^6$-(benzyloxy)-$N^2$-Boc-lysine allyl ester, k) adding trifluoro acetic acid to the (L)-$N^6$-methyl-$N^6$-(benzyloxy)-$N^2$-Boc-lysine allyl ester to form a solid intermediate and adding the solid intermediate to (L)-N-(2-(benzyloxy)benzoyl) serine and 2-ethoxy-1-ethoxycarbonyl-1,2-dihydroquinoline to produce an (L)-$N^6$-Methyl-$N^6$-(benzyloxy)-$N^2$-((L)-N-(2-(benzyloxy)benzoyl)serine)-lysine allyl ester, l) gradually adding thionyl chloride to a solution of the lysine allyl ester in anhydrous tetrahydrofuran, and purifying the resultant liquid to produce an (L)-$N^6$-Methyl-$N^6$-(benzyloxy)-$N^2$-((S)-2-(2-benzyloxy) phenyl)-2-oxazoline4-carbonyl)-lysine allyl ester m) adding morpholine and tetrakis(triphenylphosphine) palladium to the oxazoline-lysine allyl ester in anhydrous $CH_2Cl_2$ to produce an acid n) adding (L)-$N^\alpha$-((S)-3-hydroxybutyryl)-α-amino-N-(benzyloxy) caprolactam in anhydrous THF to the acid and then adding diethyl azodicarboxylate, and o) mixing the resultant material with MeOH 10% Pd/C and $H_2$ followed by co-evaporated of the MeOH with $CH_2Cl_2$ to produce an Exochelin.

2. The method of claim 1 wherein the acid is pimelic acid and the resultant end product is Exochelin 772SM(R).

* * * * *